US008529463B2

(12) United States Patent
Della Santina et al.

(10) Patent No.: US 8,529,463 B2
(45) Date of Patent: Sep. 10, 2013

(54) SYSTEMS AND METHODS FOR TESTING VESTIBULAR AND OCULOMOTOR FUNCTION

(75) Inventors: Charles C. Della Santina, Towson, MD (US); Tjen Sin Lie, Hong Kong (CN); Bryce Chiang, Somerset, NJ (US)

(73) Assignee: The Johns Hopkins University, Baltimore, MD (US)

( * ) Notice: Subject to any disclaimer, the term of this patent is extended or adjusted under 35 U.S.C. 154(b) by 211 days.

(21) Appl. No.: 12/937,985

(22) PCT Filed: Apr. 14, 2009

(86) PCT No.: PCT/US2009/040486
§ 371 (c)(1),
(2), (4) Date: Mar. 3, 2011

(87) PCT Pub. No.: WO2009/129222
PCT Pub. Date: Oct. 22, 2009

(65) Prior Publication Data
US 2011/0152711 A1 Jun. 23, 2011

Related U.S. Application Data

(60) Provisional application No. 61/124,122, filed on Apr. 14, 2008.

(51) Int. Cl.
*H04R 25/00* (2006.01)
*A61B 5/04* (2006.01)
*A61B 13/00* (2006.01)
*A61B 7/00* (2006.01)
*A61B 5/103* (2006.01)
*A61B 5/117* (2006.01)
*A61B 3/10* (2006.01)
*A61B 3/02* (2006.01)

(52) U.S. Cl.
USPC ............ 600/558; 600/25; 600/546; 600/586; 600/587; 600/595; 351/205; 351/234

(58) Field of Classification Search
USPC .................. 600/558, 595, 546, 25, 586, 587; 351/205, 234
See application file for complete search history.

(56) References Cited

U.S. PATENT DOCUMENTS 2,564,794 A * 8/1951 Shekels ......................... 351/224
3,453,998 A * 7/1969 Giglio ........................... 600/452
(Continued)

FOREIGN PATENT DOCUMENTS
WO 2005112738 A2 12/2005

OTHER PUBLICATIONS

International Search Report, International Application No. PCT/US2009/040486 (Dec. 1, 2009).
(Continued)

*Primary Examiner* — Jeffrey G Hoekstra
*Assistant Examiner* — May Abouelela
(74) *Attorney, Agent, or Firm* — Edwards Wildman Palmer LLP; Peter F. Corless; Brian R. Landry

(57) ABSTRACT

The invention relates to systems and methods for testing vestibular and oculomotor function. One aspect of the invention provides a vestibular and oculomotor function testing device including a track supported by a plurality of bearings, an engine configured to selectively displace the track, and a head coupling component coupled to the track. The head coupling component is configured to convey a movement generated by the engine to a subject's head in one or more axes.

20 Claims, 9 Drawing Sheets

(56) References Cited

U.S. PATENT DOCUMENTS

| | | | | |
|---|---|---|---|---|
| 3,737,217 | A | * | 6/1973 | Haines et al. ............... 351/224 |
| 3,782,364 | A | * | 1/1974 | Watt .............................. 600/558 |
| 4,102,564 | A | * | 7/1978 | Michael ....................... 351/210 |
| 4,278,249 | A | | 7/1981 | Forrest |
| 4,320,768 | A | | 3/1982 | Ledley et al. |
| 4,474,186 | A | * | 10/1984 | Ledley et al. ............... 600/546 |
| 4,528,989 | A | * | 7/1985 | Weinblatt ..................... 600/558 |
| 4,595,017 | A | | 6/1986 | Semenov et al. |
| 4,653,001 | A | | 3/1987 | Semenov et al. |
| 4,672,978 | A | | 6/1987 | Danto |
| 4,817,633 | A | * | 4/1989 | McStravick et al. ......... 600/595 |
| 4,848,358 | A | * | 7/1989 | Nitzan et al. ................. 600/553 |
| 5,094,521 | A | * | 3/1992 | Jolson et al. ................. 351/210 |
| 5,125,731 | A | | 6/1992 | Fiorini et al. |
| 5,161,522 | A | | 11/1992 | Clevenger |
| 5,303,715 | A | | 4/1994 | Nashner et al. |
| 5,360,010 | A | * | 11/1994 | Applegate et al. ............ 600/558 |
| 5,532,769 | A | * | 7/1996 | Miwa et al. ................... 351/205 |
| 5,823,190 | A | | 10/1998 | Voipio |
| 5,942,954 | A | | 8/1999 | Galiana et al. |
| 5,983,128 | A | | 11/1999 | Baudonniere et al. |
| 6,027,216 | A | | 2/2000 | Guyton et al. |
| 6,190,317 | B1 | * | 2/2001 | Hayafuji ....................... 600/405 |
| 6,551,214 | B1 | * | 4/2003 | Taimela .......................... 482/10 |
| 6,566,833 | B2 | | 5/2003 | Bartlett |
| 6,644,811 | B2 | | 11/2003 | Saladin |
| 6,796,473 | B2 | | 9/2004 | Purpura |
| 6,873,714 | B2 | | 3/2005 | Witt et al. |
| 7,044,602 | B2 | * | 5/2006 | Chernyak ..................... 351/208 |
| 7,234,812 | B2 | | 6/2007 | Piorkowski et al. |
| 7,285,099 | B1 | | 10/2007 | Peterka |
| 7,435,227 | B2 | | 10/2008 | Farbos |
| 7,465,050 | B2 | | 12/2008 | Migliaccio et al. |
| 7,500,752 | B2 | | 3/2009 | Nashner |
| 7,727,162 | B2 | * | 6/2010 | Peterka ......................... 600/559 |
| 7,835,820 | B2 | * | 11/2010 | Peters, II ...................... 700/245 |
| 2003/0142041 | A1 | | 7/2003 | Barlow et al. |
| 2004/0015098 | A1 | * | 1/2004 | Souvestre ..................... 600/558 |
| 2004/0083731 | A1 | * | 5/2004 | Lasker ............................. 60/645 |
| 2004/0138593 | A1 | | 7/2004 | Maher |
| 2004/0189079 | A1 | | 9/2004 | Naganuma |
| 2004/0227699 | A1 | | 11/2004 | Mitchell |
| 2005/0099601 | A1 | | 5/2005 | MacDougall et al. |
| 2006/0098087 | A1 | | 5/2006 | Brandt et al. |
| 2006/0112781 | A1 | * | 6/2006 | Kuras et al. ..................... 74/661 |
| 2007/0106170 | A1 | * | 5/2007 | Dunseath et al. ............. 600/544 |
| 2007/0121068 | A1 | | 5/2007 | MacDougall et al. |
| 2007/0177103 | A1 | | 8/2007 | Migliaccio et al. |
| 2008/0015462 | A1 | | 1/2008 | Merfeld et al. |
| 2008/0045812 | A1 | | 2/2008 | Peterka |
| 2008/0049186 | A1 | | 2/2008 | MacDougall et al. |
| 2008/0300519 | A1 | | 12/2008 | Helt, III et al. |
| 2009/0306741 | A1 | * | 12/2009 | Hogle et al. ..................... 607/54 |
| 2010/0045932 | A1 | * | 2/2010 | Shelhamer et al. ........... 351/209 |

OTHER PUBLICATIONS

Written Opinion of the International Searching Authority, International Application No. PCT/US2009/040486 (Dec. 1, 2009).

International Preliminary Report on Patentability, International Application No. PCT/US2009/040486 (Oct. 19, 2010).

G. Barnes, "Adaptation in the oculomotor response to caloric irrigation and the merits of bithermal stimulation," 29 British J. Audiology 95-106 (1995).

S.A. Bhansali & V. Honrubia, "Current status of electronystagmography testing," 120 Otolaryngol. Head Neck Surg. 419-26 (1999).

N. Colledge et al., "Magnetic resonance brain imaging in people with dizziness: a comparison with non-dizzy people," 72 J. Neurol. Neurosurg. Psychiatry 587-89 (2002).

H. Collewjin et al., "Human ocular counterroll: assessment of static and dynamic properties from electromagnetic scleral coil recordings," 59 Exp. Brain Res. 185-96 (1985).

B.T. Crane et al., "Initiation and cancellation of the human heave linear vestibulo-ocular reflex after unilateral vestibular deafferentation," 161 Ex. Brain Res. 519-26 (2005).

C.C. Della Santina et al., "Comparison of Head Thrust Test With Head Autorotation Test Reveals That the Vestibulo-ocular Reflex is Enhanced During Voluntary Head Movements," 128 Arch. Otolaryngol. Head Neck Surg. 1044-54 (Sep. 2002).

C.C. Della Santina et al., "Orientation of Human Semicircular Canals Measured by Three-Dimensional Multiplanar CT Reconstruction," 6 J. Assoc. Res. Otolaryngology 191-206 (2005).

E.G. Freedman, "Coordination of the eyes and head during visual orienting," 190 Exp. Brain Res. 369-87 (2008).

D.P. Gilchrist et al., "High acceleration impulsive rotations reveal severe long-term deficits of the horizontal vestibulo-ocular reflex in the guinea pig," 123 Exp. Brain Res. 242-54 (1998).

T.C. Hain, "Vestibular Testing," <http://www.tchain.com/otoneurology/testing/engrot.html> (Apr. 9, 2009).

G.M. Halmagyi & I.S. Curthoys, "A clinical sign of canal paresis," 45 Arch. Neurol. 737-59 (1988).

N. Heinrichs et al., "Predicting Continued Dizziness After an Acute Peripheral Vestibular Disorder," 69 Psychosomatic Medicine 700-07 (2007).

M. Hirvonen et al., "Motorized Head Impulse Rotator for Horizontal Vestibulo-ocular Reflex," 133 Arch. Otolaryngol. Head Neck Surg. 157-61 (Feb. 2007).

T.E. Hullar et al., "Responses of Irregularly Discharging Chinchilla Semicircular Canal Vestibular-Nerve Afferents During High-Frequency Head Rotations," 93 J. Neurophysiol. 2777-86 (2005).

A.A. Migliaccio et al., "The three-dimensional vestibulo-ocular reflex evoked by high-acceleration rotations in the squirrel monkey," 159 Exp. Brain Res. 433-46 (2004).

A.A. Migliaccio et al., "The Vestibulo-Ocular Reflex Response to Head Impulses Rarely Decreases after Cochlear Implantation," 26 Otology & Neurotology 655-60 (2005).

A.A. Migliaccio et al., "Axis of Eye Rotation Changes with Head-Pitch Orientation during Head Impulses about Earth-Vertical," 7 J. Assoc. Res. Otolaryngology 140-50 (2006).

L.B. Minor et al., "Horizontal vestibuloocular reflex evoked by high-acceleration rotations in the squirrel monkey," 82 J. Neurophysiol. 1254-70 (1999).

D.E. Newman-Toker et al., "Normal head impulse test differentiates acute cerebellar strokes from vestibular neuritis," 70 Neurology 2378-85 (2008).

G.D. Paige & D.L. Tomko, "Eye movement responses to linear head motion in the squirrel monkey," 65(5) J. Neurophysiol. 1170-82 (1991).

A. Palla & D. Straumann, "Recovery of the High-Acceleration Vestibulo-ocular Reflex After Vestibular Neuritis," 5 J. Assoc. Res. Otolaryngology 427-35 (2004).

H.J. Park et al., "Search-coil head-thrust and caloric tests in Meniere's disease," 125 Acta Oto-Laryngologica 852-57 (2005).

J. Peltier, "Evaluation of Vestibular Function," <http://www.utmb.edu/otoref/grnds/Vestibular-051214/Vestibular-051214.html> (Apr. 9, 2009).

S. Ramat et al., "Translational vestibulo-ocular reflex evoked by a 'head heave' stimulus," 942 Ann. N.Y. Acad. Sci. 92-113 (Oct. 2001).

D.A. Robinson, "A method of measuring eye movement using a scleral search coil in a magnetic field," 10 IEEE Trans. Biomed. Eng. 137-45 (1963).

K. Sakakura et al, "Novel Method for Recording Vestibular Evoked Myogenic Potential: Minimally Invasive Recording on Neck Exterior Muscles," 115 The Laryngoscope 1768-73 (Oct. 2005).

A. Schmid-Priscoveanu et al., "Caloric and Search-Coil Head-Impulse Testing in Patients after Vestibular Neuritis," 2/1 J. Assoc. Res. Otolaryngology 072-78 (2001).

M.C. Schubert et al., "Dynamic Visual Acuity during Passive Head Thrusts in Canal Planes," 7 J. Assoc. Res. Otolaryngology 329-38 (2006).

Skalar Medical BV, "IRIS Technology," <http://www.skalar.nl/iristech.html> (Apr. 9, 2009).

Skalar Medical BV, "IRIS Components," <http://www.skalar.nl/iriscomponents.html> (Apr. 9, 2009).

D. Straumann et al., "Transient Torsion During and After Saccades," 35(23/24) Vision Res. 3321-34 (1995).

Synapsis S.A., "The Torsio" (2000).

S. Tabak & H. Collewijn, "Human vestibulo-ocular responses to rapid, helmet-driven head movements," 102 Exp. Brain Res. 367-78 (1994).

J.R. Tian et al., "Effect of unilateral vestibular deafferentation on the initial human vestibulo-ocular reflex to surge translation," 176(4) Exp. Brain Res. 757-87 (Feb. 2007).

K.P. Weber et al., "Head impulse test in unilateral vestibular loss," 70 Neurology 454-63 (2008).

Extended European Search report for EP Application No. 09731598.0-2319/2271251 PCT/US2009040486 mailed Aug. 21, 2012.

European Official Communication for European Patent Application No. 09731598.0-1265 dated May 25, 2013.

Australian Patent Examination Report No. 1 for Australian Patent Application No. 2009236301 dated May 21, 2013.

* cited by examiner

SYSTEMS AND METHODS FOR TESTING VESTIBULAR AND OCULOMOTOR FUNCTION

RELATED APPLICATIONS

This application is a 35 U.S.C. §371 U.S. national entry of International Application PCT/US2009/040486 (WO 2009/129222) having an International filing date of Apr. 14, 2009 which claims priority to U.S. Provisional Patent Application Ser. No. 61/124,122, filed Apr. 14, 2008. The contents of these patent applications are hereby incorporated by reference in their entirety.

STATEMENT AS TO RIGHTS TO INVENTIONS MADE UNDER FEDERAL SPONSORED RESEARCH AND DEVELOPMENT

This invention was made with government support under Grant No. NIH/NIDCD K08DC006216 awarded by the National Institutes of Health. The U.S. Government has certain rights in this invention.

TECHNICAL FIELD

The invention relates to systems and methods for testing vestibular and oculomotor function.

BACKGROUND OF THE INVENTION

The vestibular labyrinth, situated in the inner ear, consists of the sensory organs that provide the dominant input for perception of head movement, perception of spatial orientation, and generation of gaze- and posture-stabilizing reflexes. In each ear, there are three roughly orthogonal semicircular canals which detect rotational head movements, as well as the otolithic endorgans, which transduce linear acceleration. A healthy vestibular system is essential for maintenance of normal vision, balance, and head orientation because the vestibular system mediates the vestibulo-ocular reflex (VOR), which stabilizes the eyes with respect to space during head movement, permitting clear and steady vision even during high frequency, high acceleration involuntary perturbations of the head and body.

A challenge for health care providers is to obtain a quick and accurate diagnosis of vestibular function in a manner that minimizes potential discomfort for the patient. Current methods of measuring vestibular sensory function are suboptimal with regard to size, expense, ease of use, patient acceptance, portability, accuracy, and the need for highly skilled operators.

One of the current standard methods of vestibular function assessment is the caloric test. This test involves irrigating the patient's ear with water at a higher or lower temperature relative to body temperature, creating convection currents in the ipsilateral horizontal semicircular canal, which in turn elicit measurable eye movements. Eye movement responses are typically measured using electro-oculography, which only provides an approximation to horizontal eye angular position. This test is often uncomfortable for the patient, and therefore can fail due to patient intolerance.

The caloric test can only provide information regarding the function of one portion of the inner ear (i.e., the horizontal semicircular canal) and cannot provide information regarding the function of other inner ear labyrinth sensors (i.e., the anterior semicircular canals, posterior semicircular canals, utricle, or saccule). The caloric test is limited to testing only low-frequency VOR performance and therefore cannot accurately assess VOR performance of the high acceleration, high frequency transient head movements for which the VOR is most important to stabilize gaze. The apparatus for caloric testing requires a highly skilled operator.

Another current standard method of vestibular function assessment is the rotary chair test. The apparatus for this test comprises a rotating motor atop which the patient is seated in a chair. The motor generates whole-body rotations and a means for measuring eye movement responses used to assess VOR function. This allows examination of vestibular responses to higher frequency head movements than the caloric test, but it is still limited to head accelerations and frequencies lower than those for which the VOR typically stabilizes gaze in healthy subjects. As the chair must move the subject's entire body, high torque, high power motors are required, making the rotary chair test apparatus very expensive to build, install, and maintain, as well as large and potentially dangerous. A highly skilled technician is required to perform rotary chair testing. Despite the cost, size, and complexity, a typical rotary chair apparatus only measures function of the horizontal semicircular canals, providing no information about the other sensors within the inner ear labyrinth.

Attempts to overcome the shortcomings of caloric and rotary chair tests led to the use of head-on-body rotations to impart high acceleration, high frequency head movement stimuli to probe VOR performance without the expense and space required for a rotary chair. Manual head thrusts (quick, transient, small amplitude head-on-body rotations) can be administered to the patient by a trained examiner. This involves the examiner gripping the patient by the head and turning the head at a high acceleration to evoke the VOR. Eye movements are typically recorded using a magnetic, electrical, or video system. Manually applied head rotations generated by a human examiner are highly variable from trial to trial, reducing the yield of this assessment method.

Accordingly, there is a need for a device that enables health care providers of various training to uniformly administer head impulse testing without the need for substantial commitment of capital and floor space.

SUMMARY OF THE INVENTION

The invention relates to systems and methods for testing vestibular and oculomotor function.

One aspect of the invention provides a vestibular and oculomotor function testing device including a track supported by a plurality of bearings, an engine configured to selectively displace the track, and a head coupling component coupled to the track. The head coupling component is configured to convey a movement generated by the engine to a subject's head in one or more axes.

This aspect can have a variety of embodiments. The device can include an oculographic device configured to record the subject's eye orientation and movement. The oculographic device can be a video-oculographic device. The video-oculographic device can include a camera and an analysis module in communication with the camera for analyzing movement of the subject's eyes. The video-oculographic device can include one or more markers for affixation to the subject's head. The analysis module can be configured to correct partial decoupling of the subject's head from the camera through analysis of motion of the one or more markers. The oculographic device can be a search coil. The oculographic device can be an electro-oculographic device.

The testing device can include a device configured to record the subject's myogenic potentials. The testing device can include a device configured to record the subject's neurogenic potentials.

The engine can be an electric motor. The electric motor can be a stepper motor, a servomotor, or a linear actuator. The engine can be a hydraulic or pneumatic piston.

The head coupling component can be coupled to the subject's head by a bite block, a helmet, or a constellation of head fixation pads and posts.

The device can include one or more angle-adjustable connectors configured to facilitate rotation of the subject's head in a plurality of axes. The device can include control means for selectively actuating the engine. The engine can include a feedback sensor. The vestibular and oculomotor function testing device can be mounted on a portable stand. The track can be a curved track or a straight track. The track can be sized such that the track will disengage from the engine before an unsafe amount of movement occurs. The device can include a motion sensor coupled to the head coupling component. The device can include one or more additional tracks supported by one or more additional sets of bearings.

Another aspect of the invention provides a method for eliciting vestibular function in a subject. The method includes providing a vestibular and oculomotor function testing device including a track supported by a plurality of bearings, an engine configured to selectively displace the track, and a head coupling component coupled to the track, the head coupling component configured to convey a movement generated by the engine to a subject's head in one or more axes; positioning the subject in contact with the head coupling component; instructing the subject to fixate or track one or more targets; and selectively actuating the engine to convey a movement to the subject's head.

Another aspect of the invention provides method for testing vestibular and oculomotor function in a subject. The method includes providing a vestibular and oculomotor function testing device including a track supported by a plurality of bearings, an engine configured to selectively displace the track, and a head coupling component coupled to the track, the head coupling component configured to convey a movement generated by the engine to a subject's head in one or more axes; positioning the subject in contact with the head coupling component; instructing the subject to fixate or track one or more targets; selectively actuating the engine to convey a movement to the subject's head; measuring vestibular and oculomotor function; and capturing movement of the subject's head with a motion sensor.

This aspect can have a variety of embodiments. The method can include repositioning the vestibular and oculomotor function testing device to convey movement along another axis, selectively actuating the engine to convey one or more additional movements, and measuring vestibular and oculomotor function. The method can include producing a diagnostic report based on the subject's measured vestibular and oculomotor function. The movements imposed on the subject's head by the vestibular and oculomotor function testing device are of sufficient acceleration and velocity to selectively stimulate function of an individual excited semicircular canal by inhibiting its coplanar semicircular canal in an opposite ear.

The step of instructing the subject to fixate or track one or more targets can include instructing the subject to visually fixate a series of targets presented at different positions. The step of instructing the subject to fixate or track one or more targets can include instructing the subject to visually track a moving target. The step of instructing the subject to fixate or track one or more targets can include instructing the subject to visually fixate a target moving along the naso-occipital axis. The step of instructing the subject to fixate or track one or more targets can include instructing the subject to visually fixate upon a display on which a series of high contrast bands moves. The step of instructing the subject to fixate or track one or more targets can include instructing the subject to visually fixate a target while the brightness of ambient light is modulated. The step of instructing the subject to fixate or track one or more targets can include instructing the subject to indicate the identity and orientation of a character or other mark presented on a display while the subject's head is stationary and while the subject's head is moved by the engine. The one or more targets can be presented on an electronic display.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein.

DEFINITIONS

The instant invention is most clearly understood with reference to the following definitions:

As used in the specification and claims, the singular form "a," "an," and "the" include plural references unless the context clearly dictates otherwise.

A "subject" shall be understood to include any mammal including, but not limited to, humans. The term "subject" specifically includes primates.

A "health care provider" shall be understood to mean any person providing medical care to a patient. Such persons include, but are not limited to, medical doctors (e.g. family practitioners and otolaryngologists), physician's assistants, nurse practitioners (e.g. an Advanced Registered Nurse Practitioner (ARNP)), nurses, residents, interns, medical students, or the like. Although various licensure requirements may apply to one or more of the occupations listed above in various jurisdictions, the term health care provider is unencumbered for the purposes of this patent application.

DETAILED DESCRIPTION

The invention relates to systems and methods for testing vestibular and oculomotor function. The invention is particularly useful in the implementation of the head impulse in one or more axes, head heave, and head surge tests for vestibular and oculomotor function.

The invention provides several advantages over existing practices. Embodiments of the invention are compact in size compared to industry standard rotary chairs. Embodiments of the invention are capable of individually testing the function of each of the six semicircular canals and four otolithic endorgans with high accuracy and repeatability. Embodiments of invention can quickly switch between conveying movement along axes of rotation and translation. Embodiments of the invention are able to measure eye movement responses in three dimensions with a non-contact video technique while compensating for head-versus-camera decoupling. Embodiments of the invention are designed to be incapable of harming a subject by moving beyond a predetermined range of head movement and acceleration. Embodiments of the invention enable a health care provider to conduct a comprehensive assessment of vestibular and oculomotor functions including angular and linear VOR, saccades, smooth pursuit, optokinetic responses, vergence, alignment, pupil reflexes, dynamic visual acuity, and gaze stability during head movement.

The Head Impulse Test

Figure 1:
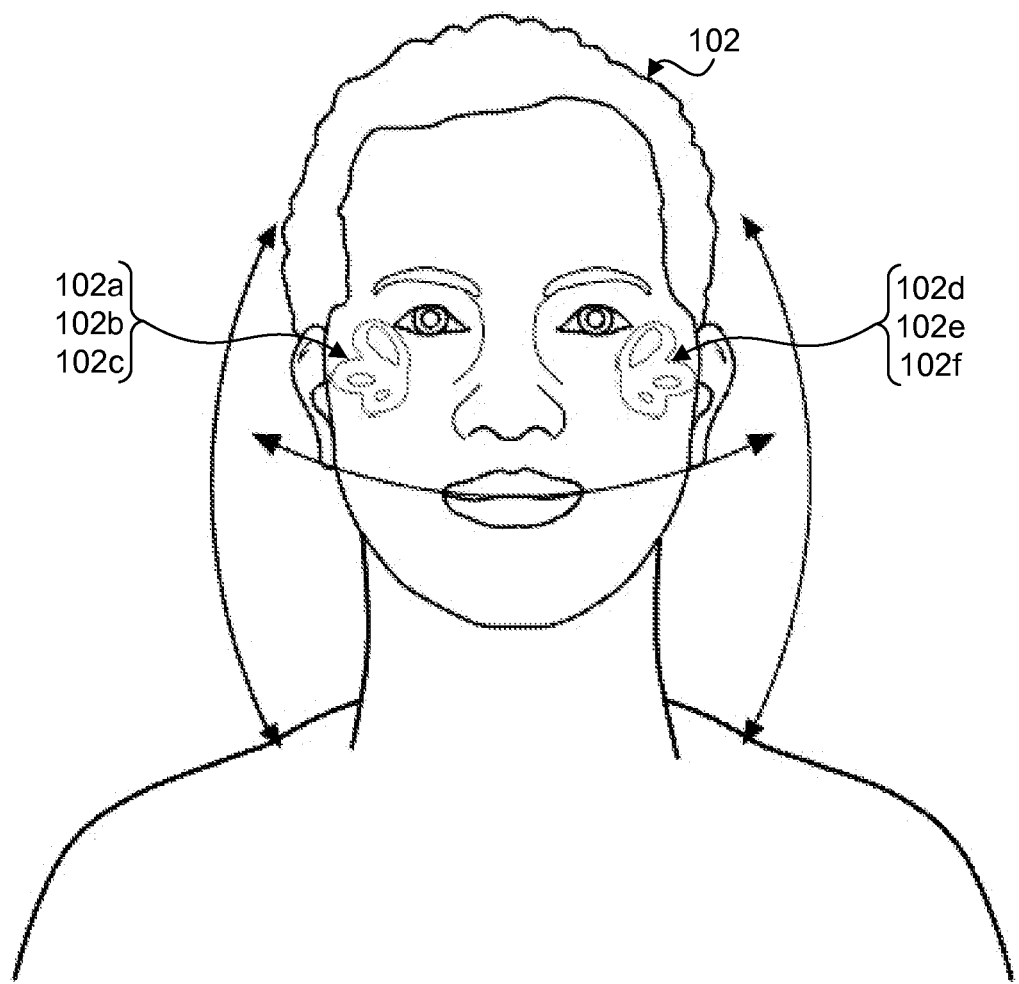
FIG. 1 depicts the axes of movement of a subject's head during the head impulse test.

The angular vestibulo-ocular reflex (VOR) stabilizes gaze to reduce image motion on the retina during rotational head movement. Angular VOR function can be measured with the head impulse test in which the subject's head is rapidly manipulated as depicted in FIG. 1. In subjects 102 with normal angular VOR function mediated by healthy semicircular canals 104a-f, the eyes remain fixated on a target as the head is rotated. Subjects with abnormal angular VOR function are unable to maintain fixation on a target during rotation, requiring a corrective gaze shift once the head stops moving. This test can be selectively applied to assess the function of each of the six semicircular canals individually, by exploiting the fact that high acceleration head rotations about the axis of one pair of semicircular canals selectively excites one semicircular canal while effectively silencing output from the other, making the VOR-mediated eye movement response an assay of the function of the excited semicircular canal alone. The head impulse test is described in a variety of publications including G. M. Halmagyi & I. S. Curthoys, "A clinical sign of canal paresis," 45 *Arch. Neurol.* 737-39 (1988).

The Head Heave Test

The linear VOR stabilizes gaze to reduce image motion on the retina during translational head movement. Linear VOR function can be measured with the head heave test in which the subject's head is rapidly translated along the interaural axis. In subjects with normal linear VOR function mediated by healthy otolithic endorgans, the eyes remain fixated on a target as the head is translated. Subjects with abnormal VOR function are unable to maintain fixation on a target during translation, requiring a corrective gaze shift once the head stops moving. The head heave test is described in a variety of publications including S. Ramat et al., "Translational vestibulo-ocular reflex evoked by a 'head heave' stimulus," 942 Ann. N.Y. Acad. Sci. 95-113 (October 2001).

The Head Surge Test

Linear VOR function can also be measured with the head surge test in which the subject's head is rapidly translated along the naso-occipital axis. In subjects with normal linear VOR function mediated by healthy otolithic endorgans, the eyes remain fixated on a target as the head is translated. Subjects with abnormal VOR function are unable to maintain fixation on a target during translation, requiring a corrective gaze shift once the head stops moving. The head surge test is described in a variety of publications including J. R. Tian et al, "Effect of unilateral vestibular deafferentation on the initial human vestibulo-ocular reflex to surge translation," 176(4) Exp Brain Res. 575-87 (February 2007).

Vestibular and Oculomotor Function Testing Device

Figure 2A:
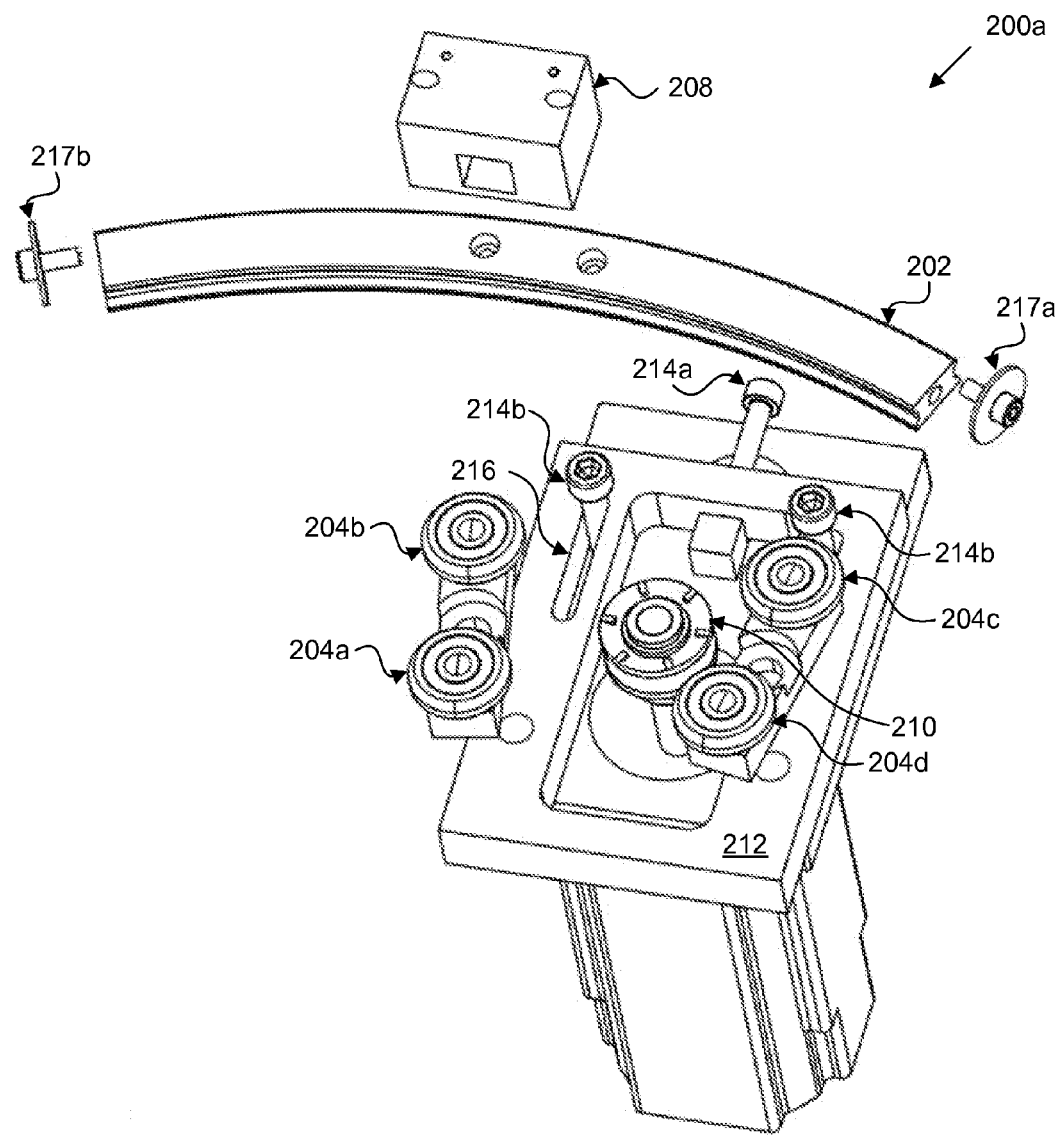
FIG. 2A depicts an exploded perspective view of a vestibular and oculomotor function testing device according to one embodiment of the invention.

Referring now to FIG. 2A, an exploded view of a vestibular and oculomotor function testing device 200a is provided. The testing device 200a includes a track 202 supported by a plurality of bearings 204a-d. In some embodiments, a plurality of tracks can be coupled to reduce undesired motion in directions other than the desired axes of motion. An engine 206 selectively displaces the track 202. A head coupling component 208 is coupled to the track 202 to convey a controlled transient, sinusoidal, or other movement generated by the engine 206 to a subject's head. The track 202 can be a curved track 202a (e.g. an arc or a circle) as depicted in FIG. 2A or can be straight track 202b as depicted in FIG. 2E.

Track 202 and bearings 204a-d can be designed to mate and thereby prevent loss or undesired movement of track 202. For example, the curved sides of track 202 can include one or more grooves that interact with the geometry of bearings 204a-d.

Engine 206 can be any mechanical device capable of producing a force in response to an input. In some embodiments, engine 206 is an electrical motor such as stepper motor or servomotor, or linear actuator. In other embodiments, engine 206 is a pneumatic or hydraulic piston or turbine. Preferably, engine 206 is capable of fast actuation to rapidly displace track 202 a defined distance.

In one embodiment, the testing device 200a moves the subject's head for about 120 milliseconds in each direction, with about 60 milliseconds dedicated to an acceleration of about 3,000° per second per second and about 60 milliseconds for deceleration of about −3,000° per second per second. This movement results in about 15° of head rotation about a given axis at about 1 meter per second of peak linear track velocity. Such speeds are sufficient to identify a difference between responses of healthy subjects and subjects with inadequate function of the angular VOR. In this embodiment, the engine and means for coupling engine movement to the track are designed so as to generate sufficient torque to move the head at the desired acceleration, but insufficient torque to injure the subject.

Engine 206 and track 202 can be coupled by a variety of means. In some embodiments, engine 206 is coupled to a gear and track 202 includes a plurality of teeth in contact with the gear. A transmission or one or more gears can be positioned between engine 206 and track 202 to facilitate the appropriate speed and/or torque.

In another embodiment depicted in FIG. 2A, rubber wheel 210 is rotated by engine 206. Rotation of rubber wheel 210 is coupled by friction to displace track 202. The use of a rubber wheel 210 enhances the safety of the testing device 200a as any significant resistance will cause the rubber wheel 210 to slip, thereby preventing the subject's head from being forcibly rotated.

Bearings 204 can be mounted on a plate 212, which is adjustably coupled to engine 206 by fasteners 214a-c. One more fasteners 214 can be located within one or more slots 216 that allow for the plate 212 to slide in a single direction with respect to engine 206 and/or rubber wheel 210. Fasteners 214 can, in some embodiments, be threaded fasteners such as screws, bolts, and the like.

Although engine 206 can be actuatable to displace track 202 to a set position, the testing device 200a can include additional features to prevent undesired displacement of track 202, thereby preventing rotation of the subject's head beyond a safe range of motion. In embodiments in which the track 202 is an arc or a straight track, the engine 206 (and, in some embodiments, rubber wheel 210) will no longer engage the curved track 202 once the curved track 202 is moved beyond a certain point. While this is sufficient to protect the subject from injury it may still be undesirable to have the curved track 202 disengage from bearings 204 and engine 206. Accordingly, some embodiments include stoppers 217a, 217b on one or more ends of the track 202. In some embodiments, stoppers 217 are washers attached to track 202 by screw, bolts, rivets, and the like.

Incorporation of Oculographic Devices and Systems

The vestibular and oculomotor function testing device 200 described herein can be combined and/or used in conjunction with various oculographic devices and systems. The oculographic devices and systems record the movement of each eye in one to three dimensions relative to the subject's head and compute parameters characterizing the dynamics of the angular VOR and/or linear VOR (e.g., velocity gain, acceleration gain, latency, peak velocity, spectrum, etc.). The oculographic devices and systems can also display and/or record the data and computed parameters and generate one or more reports suitable for use in clinical diagnostic or research laboratory settings.

Figure 2B:
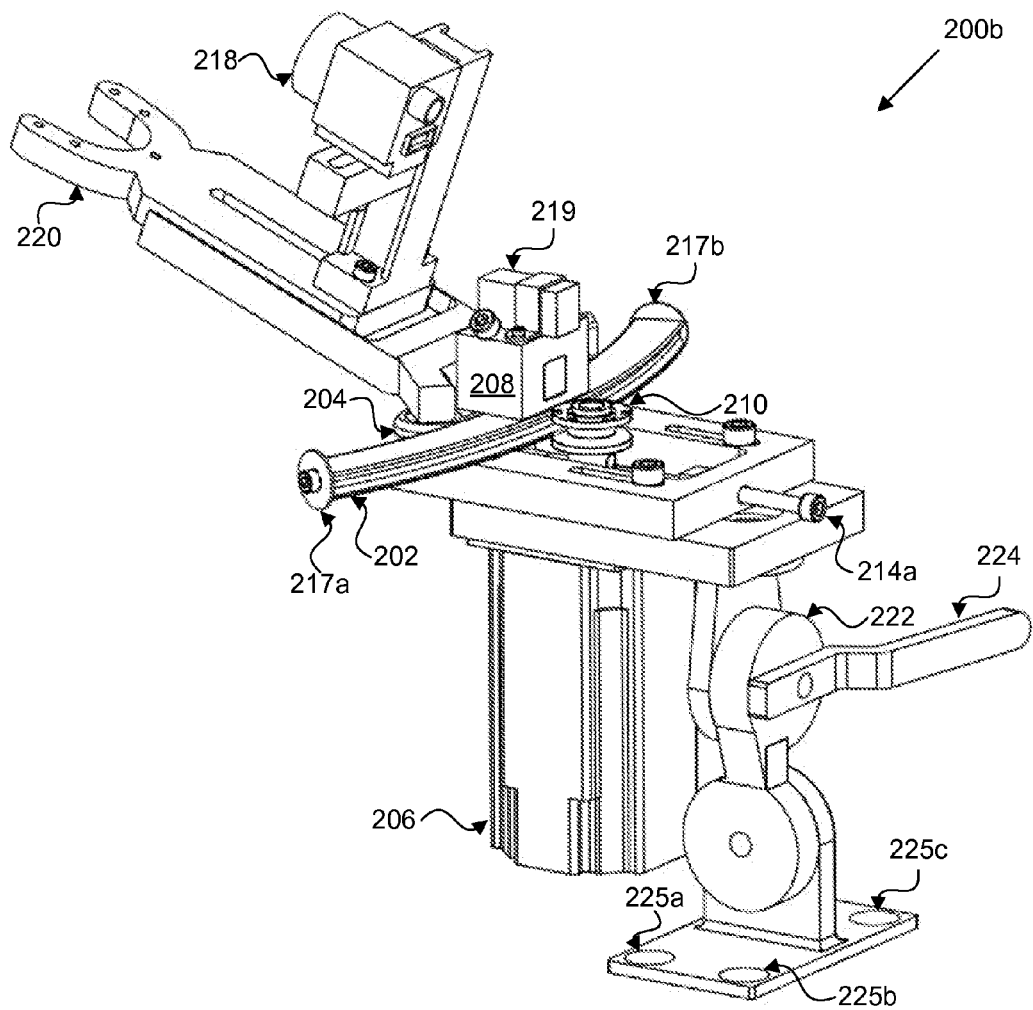
FIG. 2B depicts a perspective view of a vestibular and oculomotor function testing device including a video-oculography device according to one embodiment of the invention.

For example, referring to FIG. 2B, an exemplary vestibular and oculomotor function testing device 200b includes a video-oculography device 218. A variety of video-oculography devices are currently available and are described in publications such as U.S. Pat. Nos. 7,044,602; 7,234,812; 7,465,050; and U.S. Patent Application Publication Nos. 2004/0227699; 2006/0098087; and 2007/0177103. The video-oculography device 218 can include a camera (depicted in FIG. 2B). Video-oculography devices are available from Skalar Medical BV of Delft, The Netherlands.

In other embodiments, a search coil is used to track eye movement. Search coils can be either implanted, affixed to the eye, or incorporated within a contact lens. Search coils are described in publications such as H. Collewijn et al., "Human ocular counterroll: assessment of static and dynamic properties from electromagnetic scleral coil recordings," 59 *Exp. Brain Res.* 185-96 (1985); D. P. Gilchrist et al., "High acceleration impulsive rotations reveal severe long-term deficits of the horizontal vestibulo-ocular reflex in the guinea pig," 123 *Exp. Brain Res.* 242-54 (1998); L. B. Minor et al., "Horizontal vestibuloocular reflex evoked by high-acceleration rotations in the squirrel monkey," 82 *J. Neurophysiol.* 1254-70 (1999); G. D. Paige & D. L. Tomko, "Eye movement responses to linear head motion in the squirrel monkey," 65(5) *J. Neurophsiol.* 1170-82 (1991); and D. A. Robinson, "A method of measuring eye movement using a scleral search coil in a magnetic field," 10 *IEEE Trans. Biomed. Eng.* 137-45 (1963). Scleral search coils are available from Skalar Medical BV of Delft, The Netherlands.

In still other embodiments, electro-oculographic devices are used to track eye movement. Electro-oculographic devices are in publications such as U.S. Pat. Nos. 4,320,768; 4,474,186; 4,595,017; 4,653,001; and 5,823,190.

Additionally or alternatively, the testing device can include a device configured to record the subject's myogenic and/or neurogenic potentials as a proxy for vestibular and oculomotor response. Devices for recording myogenic potential such as electromyographs (EMGs) are known to those of skill in the art and are described in publication such as Koichi Sakakura et al., "Novel Method for Recording Vestibular Evoked Myogenic Potential: Minimally Invasive Recording on Neck Extensor Muscles," 115 The Laryngoscope 1768-73 (October 2005). Neurogenic potential can be measured with various electroencephalography (EEG) and/or magnetoencephalography devices known to those of skill in the art.

One or more motion sensors 219 (e.g. gyroscopes and accelerometers) can be coupled to head coupling component 208 to measure the head movements induced by engine 206. In embodiments incorporating a magnetic search coils, sensor 219 can be an additional magnetic coil coupled to head coupling component 208.

Each of the oculography devices described herein can include one or more analysis modules configured to record and analyze movement of the subject's eyes. The analysis module can detect and calculate data measuring oculomotor function (e.g., angular and linear VOR, saccades, smooth pursuit, optokinetic responses, vergence, and alignment), pupil reflexes, and dynamic visual acuity and gaze stability during head movement. Various data processing methods are described in publications such as D. Straumann et al., "Transient Torsion During and After Saccades," 35(23/24) Vision Res. 3321-34 (1995).

In some embodiments, one or more markers are affixed to the subject's head. These markers are identified by the analysis module and allow the analysis module to correct a partial decoupling of the subject's head from the camera through analysis of motion of one or more of the markers.

Head Coupling Component

Head coupling component 208 is configured to convey the movement generated by engine 206 to a subject's head. Still referring to FIG. 2B, head coupling component 208 can be or can be coupled to a bite block 220 inserted into the subject's mouth. Bite block 220 can be a hard material such as anodized aluminum or stainless steel. In some embodiments, bite block 220 is easily decoupled from testing device 200b to allow for quick replacement and sterilization of bite block 220 (e.g. through autoclaving). Bite block 220 can be wrapped in various dental impression materials known to those of skill in the art to more efficiently transfer forces from the bite block 220 to the subject's head and to protect the subject's teeth during testing.

In other embodiments, head coupling component 208 is or is coupled to a helmet worn by the subject. The helmet can include a foam and/or inflatable component and/or one or more straps to promote efficient transfer of torque and force from head coupling component 208 to the subject's head.

In another embodiment, head coupling component 208 is or is coupled to a constellation of head fixation pads and posts. Various configurations of pads and posts can be provided such as the devices in U.S. Pat. No. 4,278,249.

Angle-Adjustable Connectors

Figure 2C:
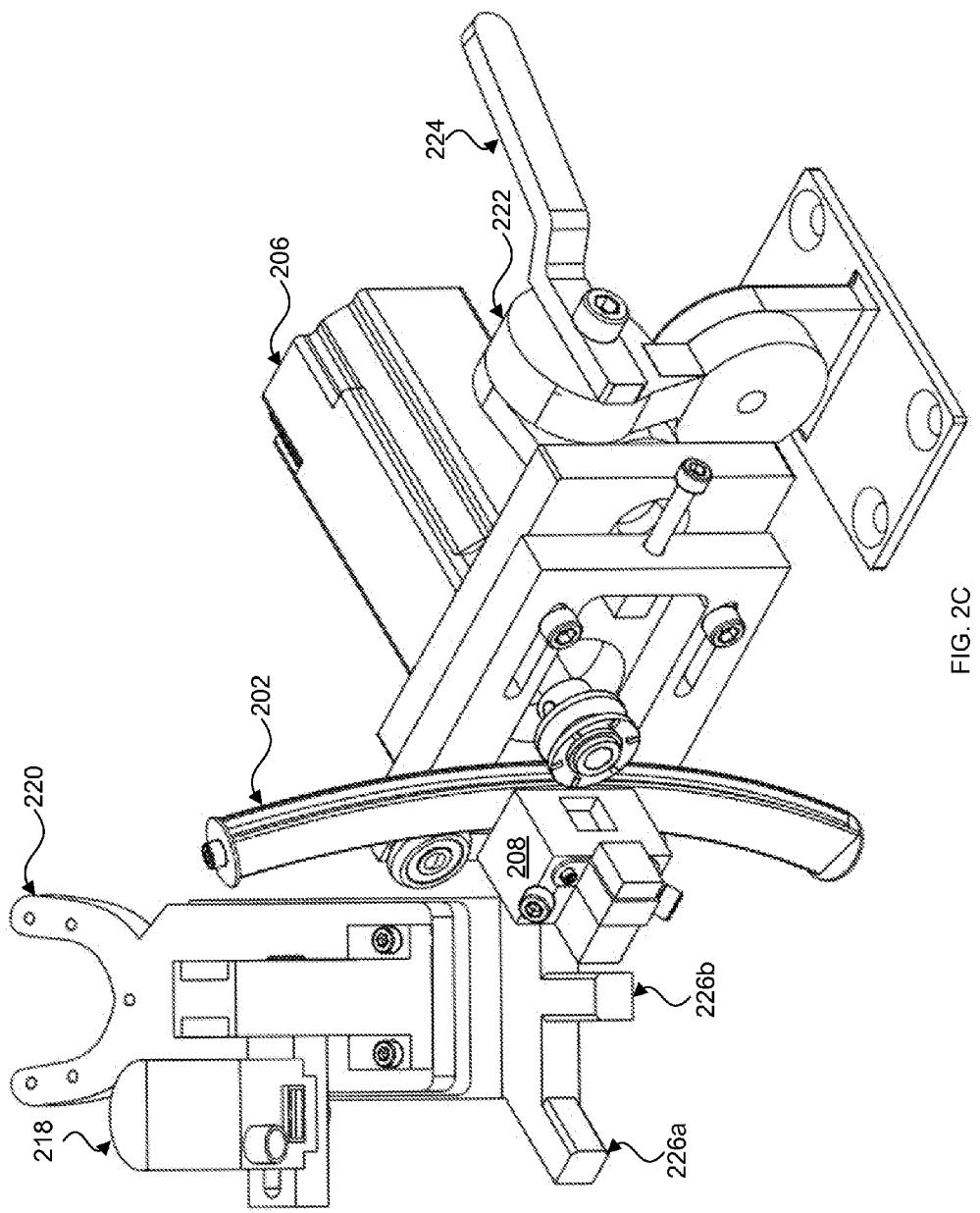
FIG. 2C depicts a perspective view of a vestibular and oculomotor function testing device rotated to convey a movement in a second axis according to one embodiment of the invention.

Still referring to FIG. 2B, the testing device 200b can be mounted on one or more angle-adjustable connectors 222, which can be locked or released with handle 224. Angle-adjustable connectors 222 allows for the quick rotation of testing device 200b to apply convey movement in another direction as depicted in FIG. 2C. Testing device 200b can be coupled to a table or a stand with fasteners (e.g., screws, bolts, nails, rivets, and the like) through holes 225. In some embodiments, testing device 200b is coupled to a portable stand (e.g., a collapsible stand or a stand including one or more wheels or casters).

As depicted in FIGS. 2B and 2C, bite block 220 includes a plurality of posts 226a, 226b, and 226c. Post 226c is not visible in FIG. 2C as it is received within head coupling component 208. The plurality of posts 226 allow for the bite block 220 to be mounted at various angles as the testing device 200b is rotated.

Bite block 220 and/or head coupling component 208 can be configured to isolate particular canals as movement is conveyed to the subject's head. For example, the horizontal semi-circular canal is oriented about 20° above earth horizontal. Bite block 220 can be angled about 20° with respect to post 226b such that when the subject places the bite block 220 in his mouth, the subject's semi-circular canal is horizontal. Likewise, posts 226a and 226c can be angled about 45° with respect to post 226b such that the axis of motion is aligned with the Left Anterior/Right Posterior (LARP) or Right Anterior/Left Posterior (RALP) axes when the appropriate post 226a, 226c is inserted into head coupling component 208. In another embodiment, the coupling 222 and bite block 220 can be fashioned to align the axis of head rotation with any other desired axis, such as the pitch or roll axes.

Figure 2D:
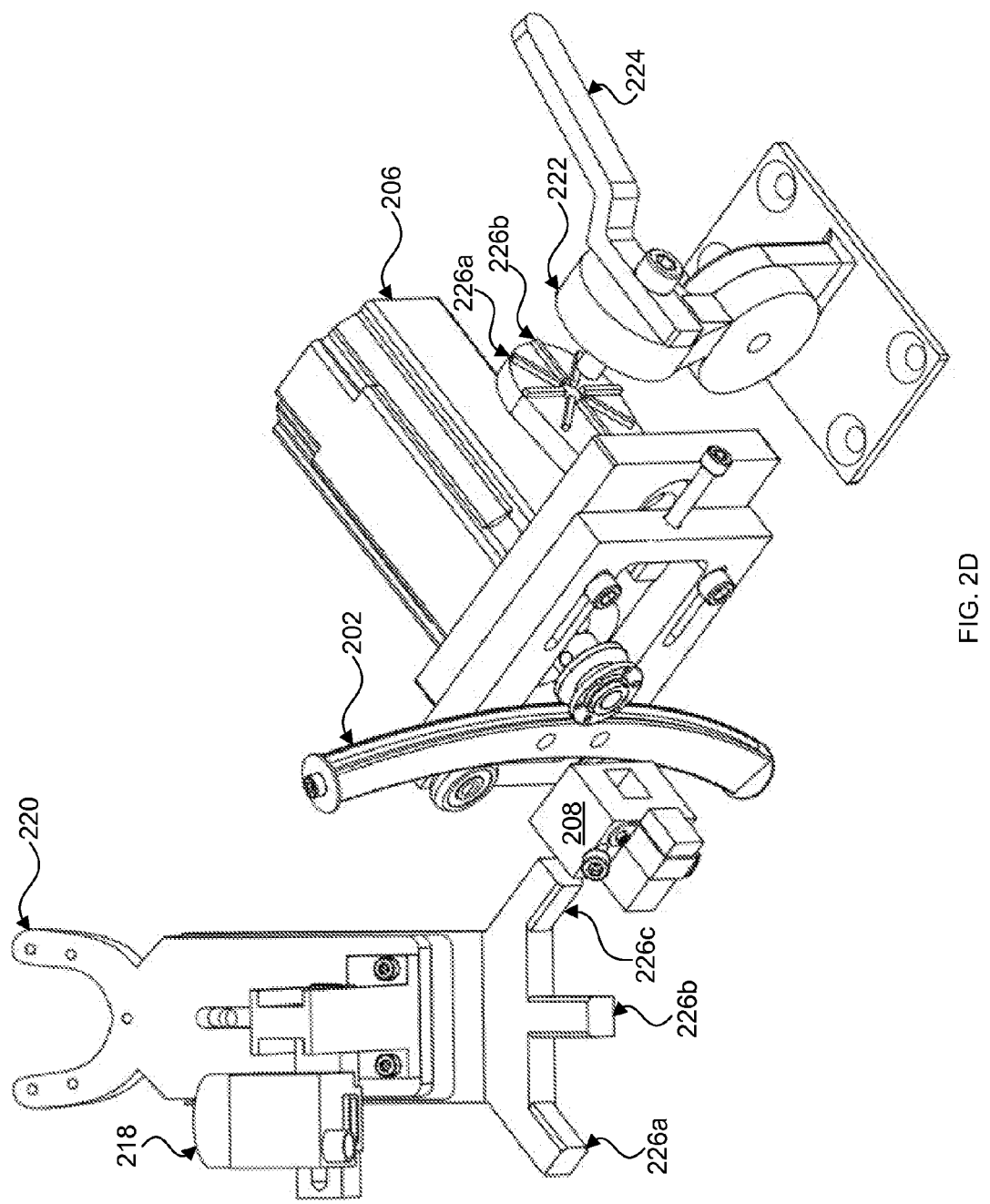
FIG. 2D depicts a semi-exploded perspective view of a vestibular and oculomotor function testing device depicting the internal structure of an angle-adjustable connector according to one embodiment of the invention.
Figure 2E:
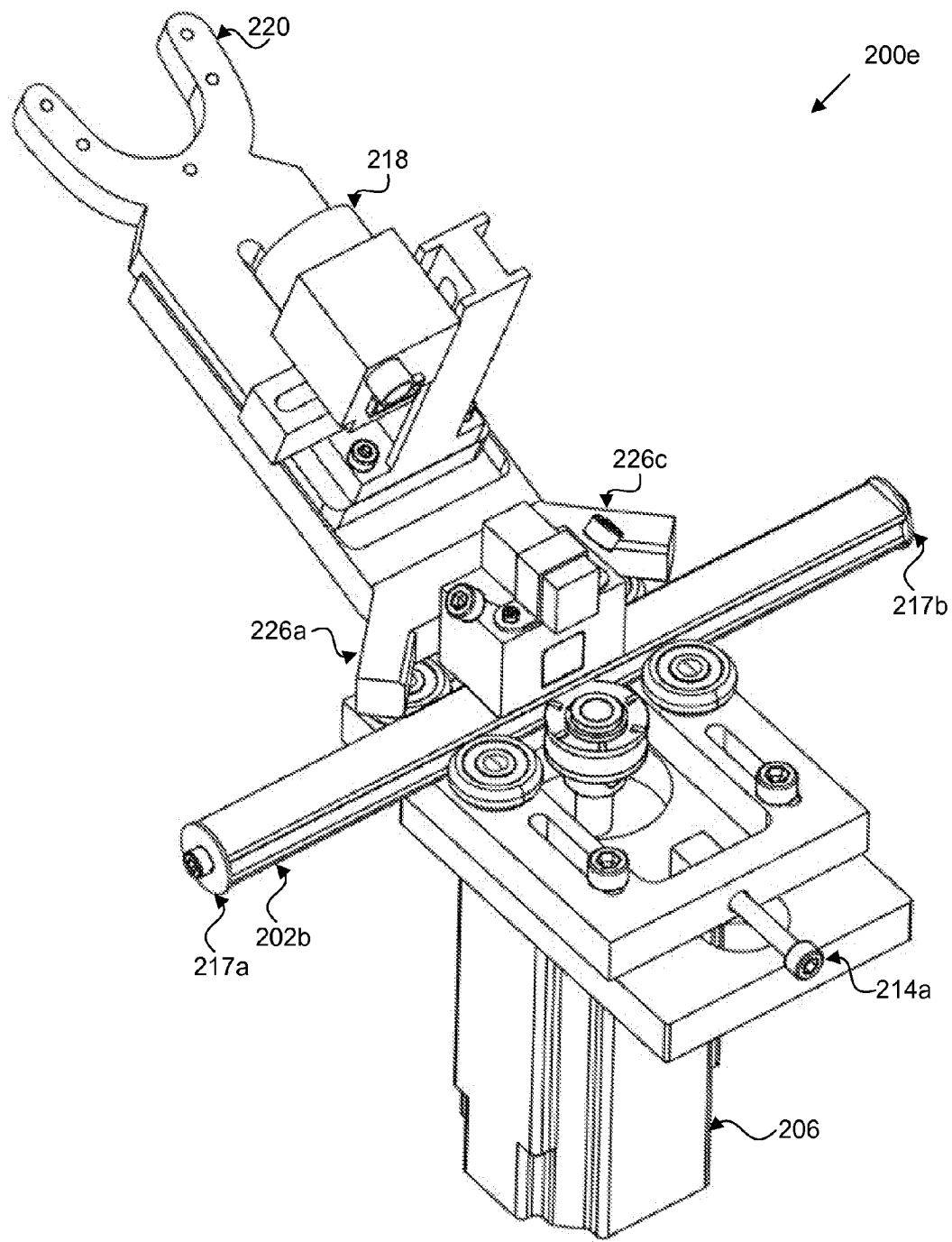
FIG. 2E depicts a vestibular and oculomotor function testing device including a straight track according to one embodiment of the invention.

Referring to FIG. 2D, the internal structure of one embodiment of an angle-adjustable connector 222 is depicted. Angle-adjustable connector 222 can include one or more detents 226a, 226b. Detents 226a, 226b interact with a complimentary geometry on the opposing member of angle-adjustable connector 222 to retain the testing device 200b at the desired angle when handle 224 is tightened. Alternatively, angle-adjustable connector 222 can hold testing device 200b solely by friction (i.e., without detents 226) when handle 224 is tightened.

Straight Track Embodiments

Referring FIG. 2E, various embodiments of invention include a straight track 202b. Straight track 202b allows the implementation of the head heave (interaural translation test). The head surge test can also be implemented with a straight track embodiment by positioning testing device 200e (e.g., by use angle-adjustable connector 222) such that track 202b moves vertically (i.e., in the direction of the subject's nose) instead of horizontally.

Track Substitution

Referring to FIGS. 2A-2D, various embodiments of the invention enable quick substitution of track 202, thereby altering the movement generated by the testing device 200b (e.g., to perform different tests or to adjust testing device 200b to the varying physical dimensions of subjects). Fasteners 214 can be loosened to allow plate 212 to move and release the grip on track 202 by rubber wheel 210 and bearings 204. Track 202 can then be removed and replaced with another track 202 having a different shape and/or radius of curvature. Plate 212 is then returned to a normal operating position and fasteners 214 are tightened.

Multi-Track Embodiments

Figure 2F:
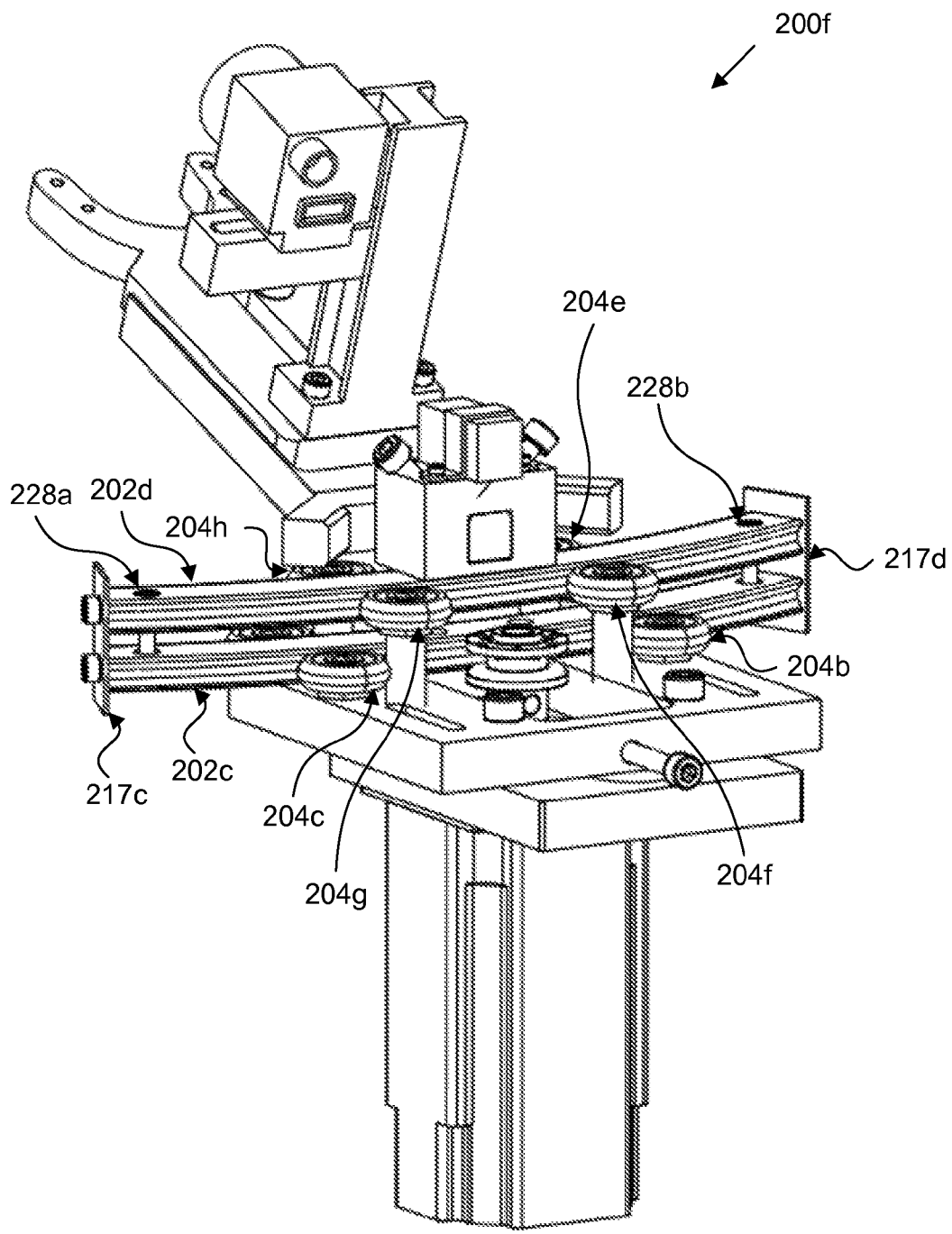
FIG. 2F depicts a vestibular and oculomotor function testing device including a multiple tracks according to one embodiment of the invention.
Figure 2G:
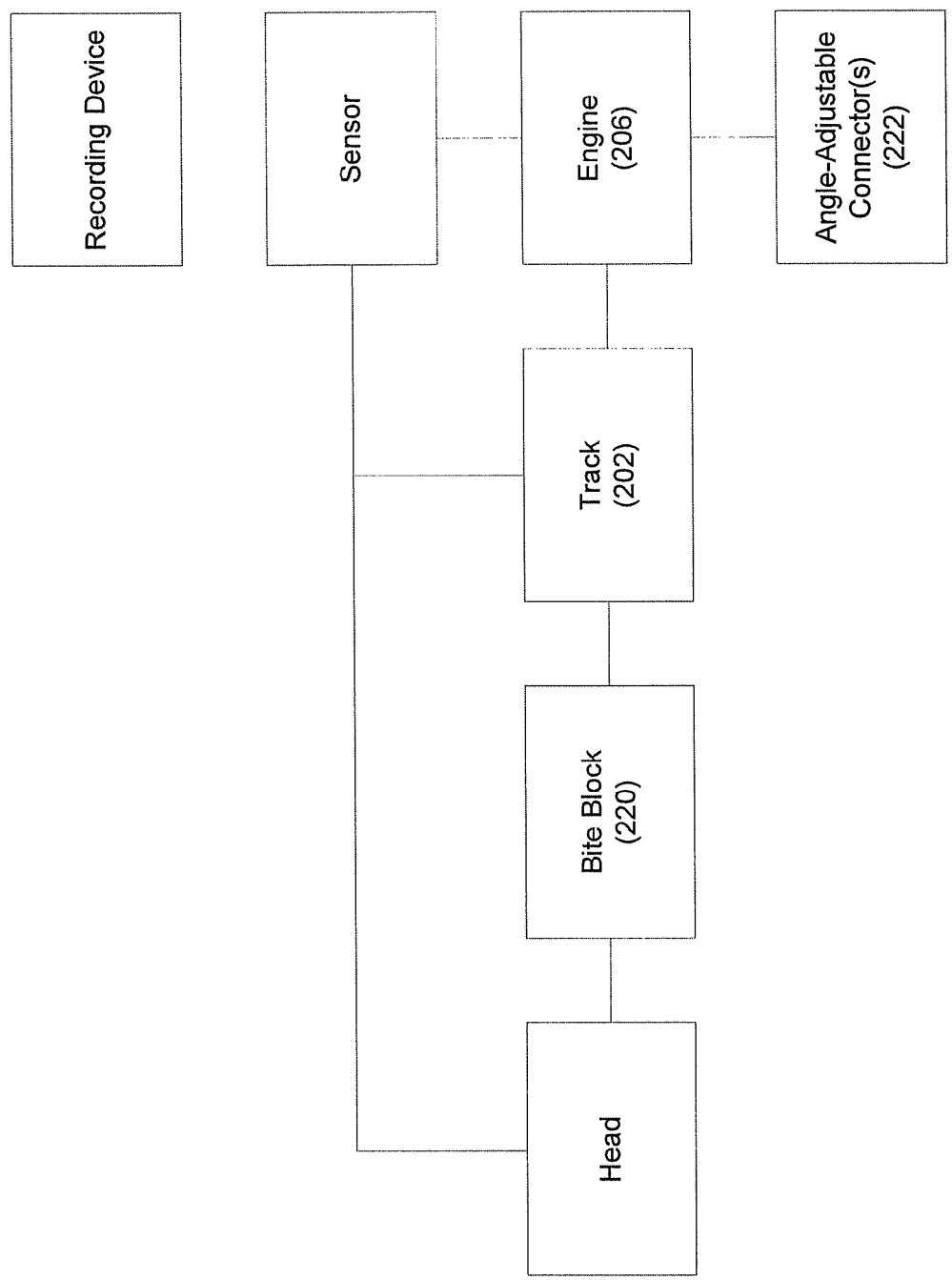
FIG. 2G depicts a schematic of a vestibular and oculomotor function testing device according to one embodiment of the invention.

Referring to FIG. 2F, some embodiments include multiple tracks 202c, 202d supported by one or more additional sets of bearings 204e-204h. The additional tracks 202 provide added support to prevent undesired support in directions other than the axes of motion. The multiple tracks 202c, 202d can be coupled in a variety of ways including stoppers 217c, 217d that span between tracks 202c and 202d. Additionally or alternatively, one or more screws, bolts, spacers, and/or posts 228a, 228b can extend through the tracks 202c, 202d.

Vestibular and Oculomotor Function Testing Methods

Figure 3:
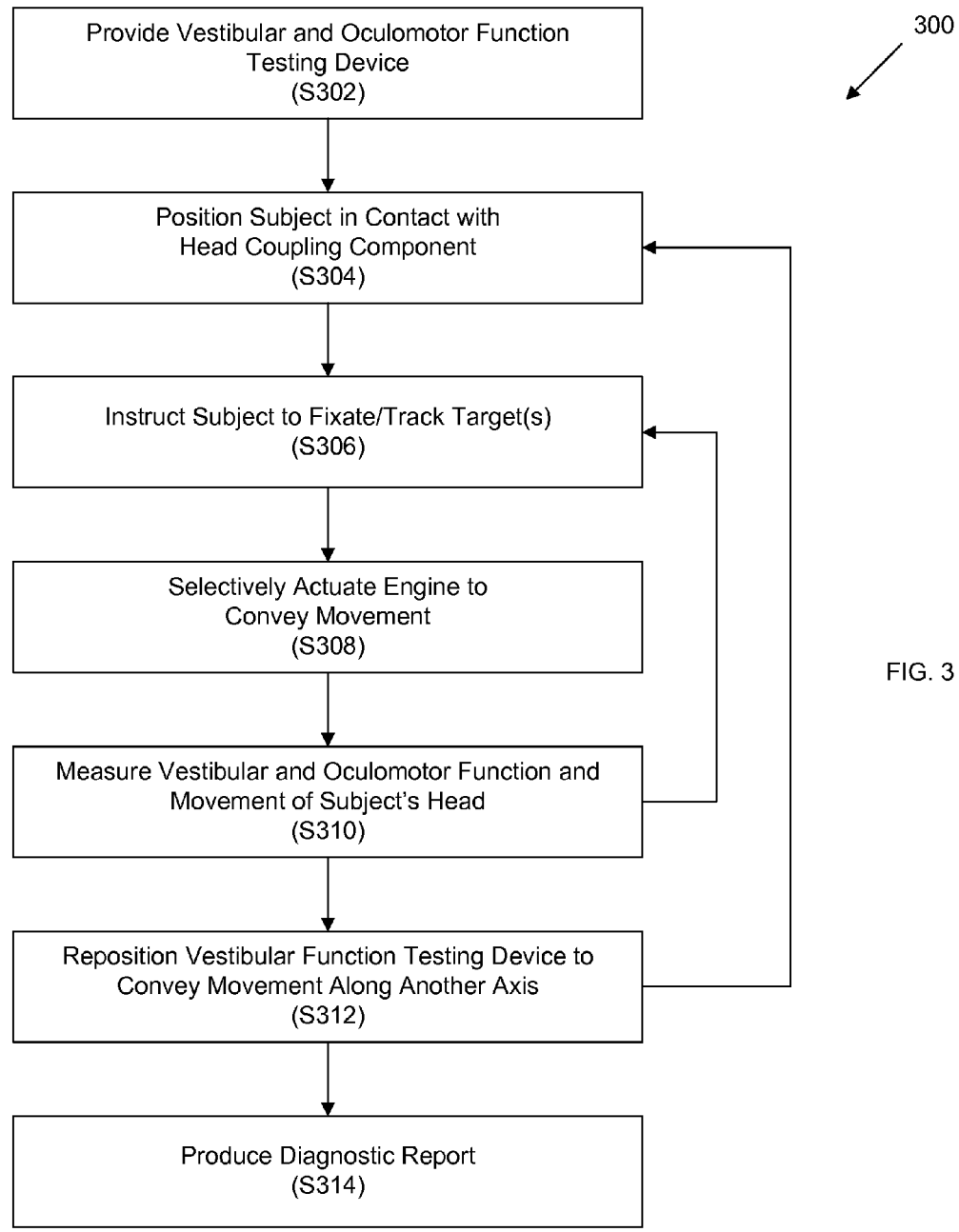
FIG. 3 depicts a method of testing vestibular and oculomotor function according to one embodiment of the invention.

Referring now to FIG. 3, a method 300 for testing vestibular and oculomotor function is provided.

In step S302, a vestibular and oculomotor function testing device is provided, for example, according to the embodiments herein.

In step S304, the subject is positioned in contact with the head coupling component 208. This step can involve having the subject 102 bite down on a bite block 220 (preferably with dental impression material). In other embodiments, the subject's head is positioned in a helmet or constellation of posts and pads attached to head coupling component 208. The subject can be a standing, seated, prone, or supine position.

In step S306, the subject 102 is instructed to fixate on or track one or more targets. To measure saccadic eye movements, the subject 102 is instructed to visually fixate a series of targets presented at different positions on a display. To measure smooth pursuit eye movements, the subject 102 is instructed to visually track a moving target presented on a display. To measure vergence eye movements, the subject 102 is instructed to visually fixate a target that moves along the naso-occipital axis. To measure optokinetic eye movements, the subject 102 is instructed to visually fixate a screen upon which a series of high contrast bands move. To measure pupillary constriction or dilation response, the subject 102 is instructed to visually fixate a target while ambient light is made more or less bright. To measure the subject's static and dynamic visual acuity, the subject 102 is instructed to indicate the identity and orientation, of a character or other mark presented on a display while the subject's head is stationary and while the subject's head is moved by the engine 206 in step S308.

In step S308, engine 206 is selectively actuated to convey a movement to the subject's head. The movements can vary in distance, velocity, and/or acceleration. In some embodiments, a movement is repeated several times to improve the reliability of measurements.

In step S310, the movement of the subject's vestibular and oculomotor function is measured (e.g. with a oculographic, EMG, or EEG device) and the movement of the subject's head is captured by one or more motion sensor (e.g. a gyroscope and/or accelerometer).

In step S312, the testing device 200 is repositioned to convey movement along another axis.

In step S314, a diagnostic report is produced (e.g. by the oculographic, EMG, or EEG device).

Control Structure

One skilled in the art will recognize that the systems and method described herein can be performed hardware, software, or a combination of both. Specifically, a control device can selectively apply appropriate amounts of electricity to motor 206 to convey movement to the subject's head. This control device can also capture data from an oculographic device 218 and motion sensor 219. This data can be associated with a particular movement.

The control device can include one or more user interfaces that allow a health care provider to control the operation of the testing device 200 and view a diagnostic report. Alternatively, the control device can be completely automated to conduct a series of tests that can be previously programmed or selected by the healthcare provider.

The control device can include an audio component (e.g. an audio out jack, speakers, headphones, and the like) and/or a video component (e.g. a display) for communicating with the healthcare provider. For example, the control device can provide audible or visual instructions to the subject regarding fixation or tracking of one or more targets as discussed herein. Likewise, the control device can project the one or more targets on the display.

INCORPORATION BY REFERENCE

All patents, published patent applications, and other references disclosed herein are hereby expressly incorporated by reference in their entireties by reference.

EQUIVALENTS

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, computers, clients, servers and the like) shown as distinct for purposes of illustration may be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

The invention claimed is:

1. A vestibular and oculomotor function testing device comprising:
    a curved track supported by a plurality of bearings;
    an engine configured to selectively displace the track;
    a bite block coupled to the track, the bite block configured to convey a movement generated by the engine to a subject's head so as to rotate the subject's head about an axis outside the device and through the subject's cranio-cervical junction region;
    one or more angle-adjustable connectors adapted and configured to facilitate rapid reorientation of the track to align its center of rotation with axes that are outside the device and through the cranio-cervical junction region of the subject's head and substantially parallel to axes of one or more semicircular canals in the subject's inner ears; and
    a sensor adapted and configured to measure and report motion of the engine, the track, and/or the head.

2. The vestibular and oculomotor function testing device of claim 1, further comprising:
    an oculographic device configured to measure the subject's vestibular and oculomotor function by capturing and comparing motion of the subject's eyes and head in one or more dimensions.

3. The vestibular and oculomotor function testing device of claim 2, wherein the oculographic device is a video-oculographic device.

4. The vestibular and oculomotor function testing device of claim 3, wherein the video-oculographic device comprises:
    one or more cameras; and
    an analysis module in communication with the camera for analyzing movement of the subject's eyes.

5. The vestibular and oculomotor function testing device of claim 4, wherein the video-oculographic device further comprises:
    one or more markers for affixation to the subject's head;
    wherein the analysis module is configured to correct partial decoupling of the subject's head from the camera through analysis of motion of the one or more markers.

6. The vestibular and oculomotor function testing device of claim 2, wherein the oculographic device is a search coil.

7. The vestibular and oculomotor function testing device of claim 2, wherein the oculographic device is an electro-oculographic device.

8. The vestibular and oculomotor function testing device of claim 1, further comprising:
    a device configured to record the subject's myogenic potentials or electro-oculographic potentials.

9. The vestibular and oculomotor function testing device of claim 1, wherein the engine is selected from the group consisting of: an electric motor, a hydraulic piston, and a pneumatic piston.

10. The vestibular and oculomotor function testing device of claim 9, wherein the electric motor is one selected from the group consisting of: a stepper motor, a servomotor, and a linear actuator.

11. A method for eliciting vestibular function in a subject, the method comprising:
    providing the vestibular and oculomotor function testing device of claim 1;
    positioning the subject in contact with the bite block;
    instructing the subject to visually fixate or track one or more targets; and
    selectively actuating the engine to convey a movement to the subject's head about axes parallel to axes of one or more of the semicircular canals of the inner ears.

12. A method for testing vestibular and oculomotor function in a subject, the method comprising:
    providing the vestibular and oculomotor function testing device of claim 1;
    positioning the subject in contact with the bite block;
    instructing the subject to visually fixate or track one or more targets;
    selectively actuating the engine to convey a movement to the subject's head about axes parallel to axes of one or more semicircular canals of the subject's inner ears;
    measuring movement of the subject's head with a motion sensor; and
    capturing movement of the subject's eyes with an oculographic device.

13. The vestibular and oculomotor function testing device of claim 1, wherein the bite block includes one or more posts, each of the one or more posts lying in a first plane that is angled with respect to a second plane defined by a portion of the bite block that is adapted and configured to be received within the subject's mouth, when seated, so as to facilitate orientation of the track's rotation axis approximately parallel to axes of horizontal semicircular canals of the subject's inner ears.

14. The vestibular and oculomotor function testing device of claim 13, wherein the bite block includes three posts spaced by about 45° within the first plane and the three posts are adapted and configured for removable coupling with the track so as to facilitate orientation of the track's rotation approximately parallel to axes of the anterior and posterior semicircular canals of subject's inner ears.

15. The vestibular and oculomotor function testing device of claim 1, further comprising:
    an electronic display adapted and configured to present stationary or moving visible targets, characters, high contrast bands or other marks as required to test oculomotor functions including saccades, smooth pursuit, optokinetic responses, vergence, alignment, pupil reflexes, dynamic visual acuity, and gaze stability.

16. A method for testing vestibular and oculomotor function in a subject, the method comprising:
providing the vestibular and oculomotor function testing device of claim 15;
positioning the subject in contact with the bite block;
instructing the subject to visually fixate or track one or more targets;
actuating the electronic display to present targets that alternate in location to facilitate testing of the subject's saccades;
actuating the electronic display to present targets that move to facilitate testing of the subject's smooth pursuit eye movements;
actuating the electronic display to present moving high-contrast bands to facilitate testing of the subject's optokinetic eye movements;
actuating the electronic display to present targets that appear to move along the naso-occipital axis to facilitate testing of the subject's vergence eye movements;
actuating the electronic display to modulate its brightness to facilitate testing of the subject's pupillary constriction or dilatation response;
instructing the subject to indicate the identity and orientation of a character or other mark presented on the display while the subject's head is stationary and while the subject's head is moved by the engine;
selectively actuating the engine to convey a movement to the subject's head about axes parallel to the axes of one or more of the semicircular canals of the inner ears;
actuating the electronic display to present characters or other marks only with the head stationary or only during head movement within a range of nonzero velocities to facilitate testing of the subject's static and dynamic visual acuity;
measuring movement of the subject's head with a motion sensor;
capturing movement of the subject's eyes with an oculographic device;
recording the subject's responses during visual acuity testing;
repositioning the vestibular function testing device to repeat testing while conveying head movement around another axis; and
producing a diagnostic report.

17. The vestibular and oculomotor function testing device of claim 1, further comprising:
one or more alternative tracks having a different radius of curvature or a different shape,
wherein the curved track can be removed and replaced with the one or more alternative tracks.

18. The vestibular and oculomotor function testing device of claim 1, wherein the track is sized such that the track will disengage from the engine before an unsafe amount of head movement occurs.

19. The vestibular and oculomotor function testing device of claim 1, further comprising:
one or more additional tracks supported by one or more additional sets of bearings, the additional tracks being adapted and configured to share the same axis of rotation and to prevent undesired head movement in directions other than a desired axis of movement.

20. The vestibular and oculomotor function testing device of claim 1, further comprising:
a rubber wheel coupled to the engine and in contact with the track, wherein rotation of the rubber wheel is translated through frictional contact to selectively displace the track.

* * * * *